United States Patent
McVenes et al.

(10) Patent No.: US 7,801,623 B2
(45) Date of Patent: Sep. 21, 2010

(54) IMPLANTABLE MEDICAL DEVICE HAVING A CONFORMAL COATING

(75) Inventors: Rick D. McVenes, Isanti, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 1015 days.

(21) Appl. No.: 11/427,625

(22) Filed: Jun. 29, 2006

(65) Prior Publication Data
US 2008/0004670 A1      Jan. 3, 2008

(51) Int. Cl.
*A61N 1/05* (2006.01)
(52) U.S. Cl. .................................... 607/116
(58) Field of Classification Search ............ 607/36, 607/37, 115, 119, 121, 116; 600/377, 381; 427/2.1, 2.24, 249.17–249.19
See application file for complete search history.

(56) References Cited

U.S. PATENT DOCUMENTS

| | | | |
|---|---|---|---|
| 4,058,430 A | 11/1977 | Suntola et al. | |
| 4,413,022 A | 11/1983 | Suntola et al. | |
| 4,603,704 A * | 8/1986 | Mund et al. | 607/116 |
| 6,015,590 A | 1/2000 | Suntola et al. | |
| 6,141,205 A | 10/2000 | Nutzman et al. | |
| 6,430,448 B1 * | 8/2002 | Chitre et al. | 607/121 |
| 6,512,940 B1 | 1/2003 | Brabec et al. | |
| 6,522,915 B1 | 2/2003 | Ceballos et al. | |
| 6,546,292 B1 * | 4/2003 | Steinhaus et al. | 607/116 |
| 6,551,873 B2 | 4/2003 | Park et al. | |
| 6,551,893 B1 | 4/2003 | Zheng et al. | |
| 6,622,046 B2 | 9/2003 | Fraley et al. | |
| 6,799,076 B2 * | 9/2004 | Gelb et al. | 607/121 |
| 6,944,489 B2 | 9/2005 | Zeijlemaker et al. | |
| 6,985,775 B2 | 1/2006 | Reinke et al. | |
| 2002/0009604 A1 | 1/2002 | Zamora et al. | |
| 2002/0026899 A1 | 3/2002 | McLaughlin et al. | |
| 2002/0055242 A1 | 5/2002 | Uhlenbrock et al. | |
| 2003/0141193 A1 | 7/2003 | Hossick-Schott | |
| 2004/0023253 A1 | 2/2004 | Kunwar et al. | |
| 2004/0064175 A1 * | 4/2004 | Lessar et al. | 607/122 |
| 2004/0077142 A1 | 4/2004 | Chao et al. | |
| 2004/0110348 A1 | 6/2004 | Ahn et al. | |
| 2004/0110391 A1 | 6/2004 | Ahn et al. | |
| 2004/0127966 A1 * | 7/2004 | Frericks et al. | 607/116 |

(Continued)

FOREIGN PATENT DOCUMENTS

EP    1 454 651 A1    9/2004

(Continued)

OTHER PUBLICATIONS

Lee, Jae P. et al., "A New Patterning Method Using Photocatalytic Lithography and Selective Atomic Layer Deposition", J Am Chem Soc, vol. 126, pp. 28-29; Published on Web Dec. 12, 2003.

(Continued)

*Primary Examiner*—Kennedy J Schaetzle
*Assistant Examiner*—Jessica Sarcione

(57) ABSTRACT

A method for manufacturing an implantable electrical medical device includes forming a conductive substrate, placing the conductive substrate in a deposition chamber; and forming a conformal coating over the conductive substrate using atomic layer deposition. In various embodiments, the conformal coating is a conductive coating and in other embodiments the conformal coating is a dielectric coating.

6 Claims, 7 Drawing Sheets

U.S. PATENT DOCUMENTS

| | | |
|---|---|---|
| 2004/0161949 A1 | 8/2004 | Yadav et al. |
| 2004/0176828 A1* | 9/2004 | O'Brien ............ 607/119 |
| 2004/0197527 A1 | 10/2004 | Maula et al. |
| 2005/0032325 A1 | 2/2005 | Bhat et al. |
| 2005/0131509 A1* | 6/2005 | Atanassoska et al. ....... 607/122 |
| 2005/0194628 A1 | 9/2005 | Kellar et al. |
| 2007/0005116 A1 | 1/2007 | Lo |
| 2007/0233217 A1* | 10/2007 | Yang et al. ............ 607/126 |
| 2007/0250142 A1* | 10/2007 | Francis et al. ............ 607/116 |

FOREIGN PATENT DOCUMENTS

| | | |
|---|---|---|
| WO | WO 2005/046470 A1 | 5/2005 |
| WO | WO 2006/094191 A2 | 9/2006 |
| WO | WO 2006/131912 A2 | 12/2006 |
| WO | WO 2007/117838 A2 | 10/2007 |

OTHER PUBLICATIONS

International Search Report for PCT/US2007/071856.

* cited by examiner

IMPLANTABLE MEDICAL DEVICE HAVING A CONFORMAL COATING

TECHNICAL FIELD

The invention relates generally to implantable medical devices and, in particular, to implantable medical devices having conformal coatings applied using atomic layer deposition.

BACKGROUND

Medical electrodes are used in conjunction with a variety of electronic implantable medical devices such as pacemakers, cardiovertor defibrillators, neurostimulators, and ECG monitors. Medical leads may carry one or more electrodes used for sensing electrical signals in the body, such as intracardiac electrogram (EGM) signals, electrocardiogram (ECG) signals, and electromyogram (EGM) signals. Electrodes are also used for delivering therapeutic electrical stimulation pulses or for delivering electrical pulses used in electrophysiological mapping or for other diagnostic purposes. Leadless electrodes may be incorporated on the housing of an implantable medical device and used for sensing and/or stimulating in combination with other leadless or lead-based electrodes.

In selecting materials for fabricating a medical electrode, considerations include the biocompatibility, electrical properties, mechanical properties, chemical stability, the radiographic visibility of the material and the electrode-tissue interfacial impedance. Known or proposed medical electrodes are fabricated with a base material formed from platinum, titanium, tantalum, stainless steel, iridium, or alloys thereof. Platinum and platinum-iridium provide good electrical and mechanical properties, are chronically biostable and are highly visible under radiography. For these reasons, platinum and platinum-iridium, though relatively costly materials, are commonly used for manufacturing medical electrodes intended for chronic implantation. The electrode base material is often coated with a porous or high surface area coating, referred to as a low polarization coating, to reduce the effects of polarization at the tissue-electrode interface, which can interfere with electrode performance. Known or proposed medical electrode coatings include platinum black, carbon black, platinum oxide, iridium oxide, and porous carbide, nitride, or carbonitride layers formed form titanium, vanadium, zirconium, niobium, molybdenum, hafnium, tantalum, iridium, platinum, and tungsten.

BRIEF DESCRIPTION OF THE DRAWINGS

Aspects and features of the present invention will be appreciated as the same becomes better understood by reference to the following detailed description of the embodiments of the invention when considered in connection with the accompanying drawings, wherein.

DETAILED DESCRIPTION

Figure 1:
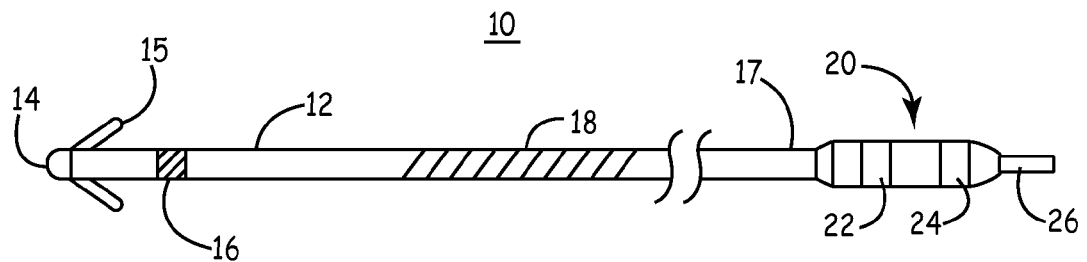
FIG. 1 is a plan view of one embodiment of a medical electrical lead.

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise noted, drawing elements are not shown to scale.

FIG. 1 is a plan view of one embodiment of a medical electrical lead. Lead 10 includes an elongated lead body 12 extending between a distal end 15 and a proximal end 17. A tip electrode 14 is provided at distal lead end 15. A ring electrode 16 is spaced proximally from tip electrode 14 and a coil electrode 18 is spaced proximally from ring electrode 16. Each electrode 14, 16 and 18 is individually coupled to an insulated conductor extending through lead body 12 to a connector 22, 24 or 26 included in proximal connector assembly 20. Proximal connector assembly 20 is adapted to be inserted in a connector bore provided in an implantable medical device for electrically connecting electrodes 14, 16 and 18 to electronics included in the IMD.

Tip electrode 14, ring electrode 16, and/or coil electrode 18 are formed having an electrode base with a conformal coating applied thereover using atomic layer deposition (ALD) methods. The term "conformal" as used herein refers to a coating being pin-hole free and uniformly covering the base substrate even when the substrate is formed with a very high aspect ratio. ALD involves placing a substrate target in a heated vacuum chamber and exposing the target to precursor gas pulses applied in rapid succession. A first precursor gas pulse produces a monolayer of the precursor on the target surface, and a second precursor gas pulse reacts with the first precursor to form an atomic monolayer. A coating or film is built up one monolayer at time by repeating the deposition cycles until a desired film thickness is reached. Some examples of atomic layer deposition methods and apparatus are disclosed in U.S. Pat. No. 4,058,430, 4,413,022, and 6,015,590.

Figure 2:
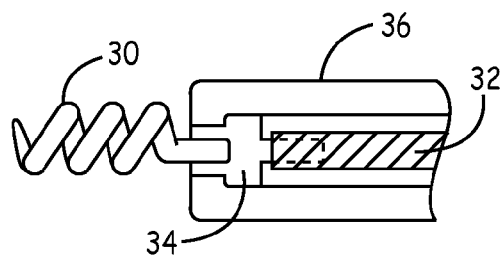
FIG. 2 is a sectional view of the distal end of an electrical medical lead provided with an active fixation electrode.

FIG. 2 is a sectional view of the distal end of an electrical medical lead provided with an active fixation electrode. Fixation electrode 30 is embodied as a helical electrode and is electrically coupled to a conductor 32 via sleeve 34. Lead-based electrodes such as fixation electrode 30 and any of the electrodes 14, 16, and 18 shown in FIG. 1 are typically electrically coupled to a welding or crimping sleeve, which is further coupled to a conductor. Conductor 32 may be provided as any wire, stranded or multifilar, coiled, or cable type conductor. Conductor 32 is coupled to sleeve 32 using any appropriate method such as welding, staking, crimping or riveting. Conductor 32 extends through lead body 36 to a connector assembly at a proximal lead body end.

The methods and materials described herein for providing a medical device having a conformal coating formed using ALD apply to fixation electrode 30 as well as any of the electrodes shown in FIG. 1 or any other electrode known for use with implantable medical device systems. Any electrode base configuration, including, but not limited to, tip electrodes, button electrodes, ring electrodes, coil electrodes, patch electrodes, as well as active fixation electrodes such as helical electrodes and "fish hook" electrodes, may be provided with a conformal coating applied using ALD.

Figure 3:
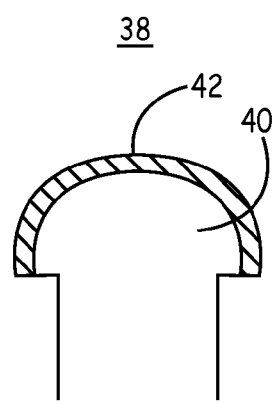
FIG. 3 is a sectional view of an electrode base provided with a conformal coating.

FIG. 3 is a sectional view of an electrode base provided with a conformal coating. Electrode 38 includes electrode base 40 and a conformal coating 42 applied to base 40 using ALD. Electrode base 40 is formed from any conductive metal or metal alloy. Conformal coating 42 is a conductive coating in some embodiments and may be provided as a conductive coating characterized by greater chemically stability than the underlying electrode base 40. Materials used for forming medical electrodes and appropriate for forming electrode base 40 include, for example, platinum, iridium, tantalum, titanium, and alloys thereof. It is contemplated, however, that electrode base 40 having conformal coating 42 may be formed from alternative metals or metal alloys that are generally considered to lack the chemical stability needed in a chronic implant environment. For example, electrode base 40 may be formed from tungsten, stainless steel, or alloys thereof.

Tungsten has good electrical properties for use as an implantable electrode. Other properties of tungsten include low cost, radiographic visibility, and high thermal conductivity. The high thermal conductivity of tungsten may act to prevent tissue heating at the electrode tissue interface during MRI procedures. However, tungsten has not been used commercially as a base material for chronically implanted medical electrodes because it is not biostable in the implanted environment and will degrade over time. A tungsten or stainless steel electrode base 40 may be formed into a chronically stable electrode 38 when provided with a conformal conductive coating 42 using ALD. As used herein, "chronic" refers to implant durations exceeding about 24 hours with the expectation that the device will generally remain implanted for days, weeks, months or years. IMDs implanted acutely may be implanted for a few minutes or hours and are generally used for diagnostic testing or performing a surgical or other clinical procedure, such as electrophysiological mapping, tissue ablation, angioplasty, imaging or other procedures. Although electrodes may be provided with a conformal conductive coating having the chemical stability needed for chronic implantation, embodiments of the present invention are not limited to electrodes or devices intended for chronic use only but may also include devices implanted acutely.

In one illustrative example, a tungsten electrode base is coated with a conformal tungsten nitride coating by ALD using a tungsten precursor source material such as bis(tert-butylimido)bis(dimethylamido)tungsten and a nitrogen precursor such as ammonia. A conductive conformal coating is applied by rapid succession of gas pulses which form an atomic monolayer in two step cycles which generally include 1) depositing a monolayer of the precursor source material, and 2) forming a nitride, carbide or carbonitride of the monolayer by applying a nitrogen and/or carbon source material.

In some embodiments, the electrode base 40 is formed with an enhanced surface area to reduce the effects of post-polarization artifacts. For example, electrode base 40 may be formed as a porous, sintered electrode. Alternatively, electrode base 40 is surface enhanced using post-processing methods such as mechanical etching or other machining processes. Conformal coating 42 is applied by ALD methods to form a uniform, pin-hole free coating even when base 40 is provided having a highly structured surface. Conformal coating 42 may be formed as a carbide, nitride or carbonitride coating. Conformal coating 42 provides chemical stability to electrode 38 for chronic implantation by providing a pin-hole free coating over a less chemically stable electrode base 40. Conformal coating 42 may be provided as conductive coating including a carbide, nitride, or carbonitride of any metal, including, but not limited to, titanium, vanadium, zirconium, niobium, molybdenum, hafnium, tantalum, iridium, platinum, and tungsten.

Figure 4:
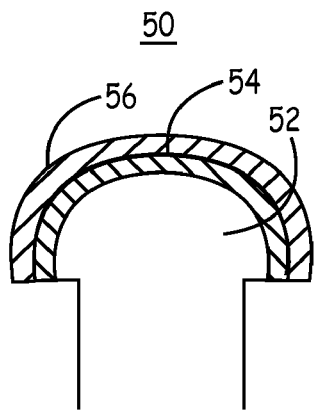
FIG. 4 is a sectional view of an electrode provided with an intermediate conformal coating applied over an electrode base.

FIG. 4 is a sectional view of an electrode 50 provided with an intermediate conformal coating 54 applied over an electrode base 52. A low polarization coating 56 is applied over conformal coating 54. In one embodiment, conformal coating 54 is provided as a conductive coating that is more chemically stable than the underlying electrode base 52. Electrode base 52 may be characterized by a low surface area making a porous, low polarization coating 56 desirable for improving electrode performance. Low polarization coating 56 may be applied by sputtering, dipping, chemical vapor deposition, or other appropriate method depending on the type of coating being applied. Low polarization coating 42 may be formed from platinum black, carbon black, a carbide, nitride or carbonitide or any other known low polarization coating.

Figure 5:
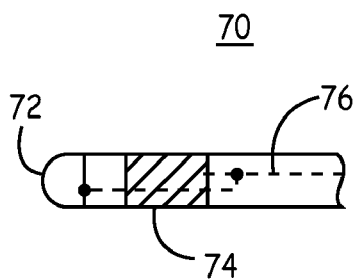
FIG. 5 is a plan view of the distal portion of a medical electrical lead having electrodes provided with a conformal coating according to another embodiment of the invention.

FIG. 5 is a plan view of the distal portion of a medical electrical lead having electrodes provided with a conformal coating according to another embodiment of the invention. Lead 70 is provided with a tip electrode 72 for delivering electrical stimulation pulses and/or sensed electrical signals and a ring electrode 74 serving as an RF shunt electrode. Tip electrode 72 may be fabricated, as described previously, having a conductive conformal coating applied over an electrode base. Tip electrode 72 may further include a low-polarization coating applied over the conductive conformal coating.

Ring electrode 74 includes a conductive electrode base and a conformal dielectric coating applied there over. The conformal dielectric coating is formed by ALD as a metal oxide or mixed metal oxide using one or more metal source precursors and an oxygen source, such as water vapor. For example, the dielectric conformal coating may be formed as a desired number of monolayers of oxides of aluminum, titanium, vanadium, zirconium, niobium, molybdenum, hafnium, tantalum, iridium, platinum, tungsten, or mixtures thereof. The monolayers may be formed as mixed oxide layers by applying two or more metal precursor sources simultaneously during a deposition cycle. Alternatively, a mixed oxide coating may be provided by applying different metal precursor pulses on alternating deposition cycles to form alternating layers of different metal oxides.

The ring electrode 74 is electrically coupled to a tip electrode conductor 76. Ring electrode 74 serves as an RF shunt electrode for shunting current induced on conductor 76 during exposure to high frequency electromagnetic interference, such as during magnetic resonance imaging (MRI) procedures, Induced high frequency signals are shunted to body tissue in contact with ring electrode 74, away from tip electrode 72. The use of a capacitor between a tip electrode and a ring electrode in a shunting assembly for a medical lead is generally disclosed in U.S. Pat. No. 6,944,489 (Zeijlemaker et al.) and U.S. Pat. No. 6,985,775 (Reinke et al.), both of which patents are incorporated herein by reference in their entirety. By providing ring electrode 74 with a conformal dielectric coating, ring electrode 74 will act as a capacitive element with the surrounding body tissue or blood to pass a portion of high frequency signals induced along conductor 76. A conductive coating may optionally be applied over the conformal dielectric coating. Ring electrode 74 acts as a high frequency filter, allowing low frequency signals, like pacing or other electrical stimulation signals and sensed electrophysiological signals to be conducted through tip electrode 72. The capacitance of ring electrode 74 is determined by the properties of the conformal dielectric layer and may be selected with consideration of the electrical impedance of the surrounding tissue or blood and tip electrode 72 to create a high pass filter having desired frequency characteristics.

Figure 6:
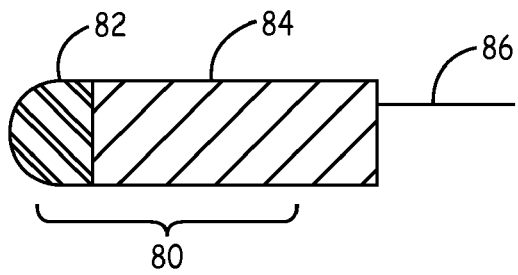
FIG. 6 is a side view of an electrode base provided with a conformal conductive coating and a conformal dielectric coating.

FIG. 6 is a side view of an electrode base provided with a conformal conductive coating and a conformal dielectric coating.? In FIG. 5, ring electrode 74 is provided as a separate structure for shunting induced signals away from tip electrode 72. In an alternative embodiment, an electrode base 80 may be provided with a conductive conformal coating over a distal tip portion 82 and a dielectric conformal coating over a proximal portion 84. A portion of high frequency signals induced on conductor 86 will be shunted through the dielectric coated portion 84, away from the conductive tip portion 82. Low frequency stimulation and/or sensing signals will be conducted through the conductive tip portion 82.

Figure 7:
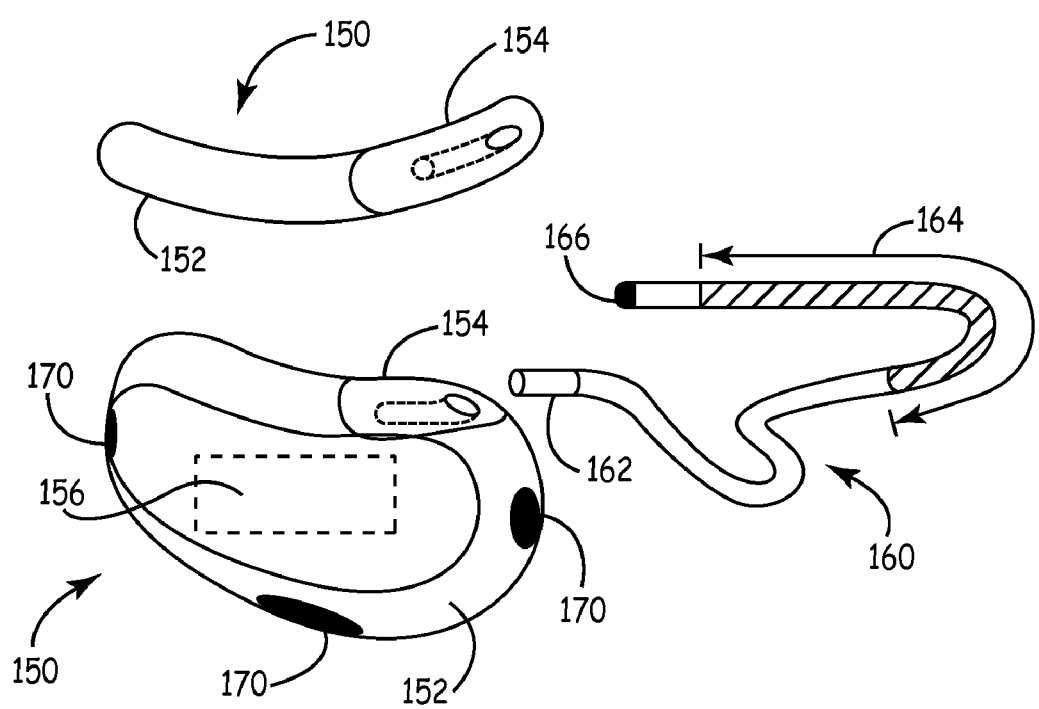
FIG. 7 is a top and plan view of an IMD incorporating electrodes disposed along the IMD housing for subcutaneously sensing and/or delivering electrical stimulation pulses.

FIG. 7 is a top and plan view of an IMD incorporating electrodes disposed along the IMD housing for subcutaneously sensing and/or delivering electrical stimulation pulses. Embodiments of the present invention include both lead-based and leadless electrodes. IMD 150 is embodied as a subcutaneous ICD. IMD 150 includes a generally ovoid housing 152 having a substantially kidney-shaped profile. Connector block 154 is coupled to housing 152 for receiving the connector assembly 162 of subcutaneous lead 160. IMD housing 150 is hermetically sealed and may be constructed of stainless steel, titanium or ceramic. Electronics module 156 enclosed in housing 152 may be incorporated on a polyamide flex circuit, printed circuit board (PCB) or ceramic substrate with integrated circuits packaged in leadless chip carriers and/or chip scale packaging (CSP). The plan view shows the generally ovoid construction of housing 152 that promotes ease of subcutaneous implant. This structure is ergonomically adapted to minimize patient discomfort during normal body movement and flexing of the thoracic musculature.

Subcutaneous lead 160 includes distal coil electrode 164, distal sensing electrode 166, an insulated flexible lead body and a proximal connector assembly 162 adapted for connection to IMD 150 via connector block 154. IMD 150 is provided with one or more housing-based electrodes forming a subcutaneous electrode array (SEA) 170. Three electrodes positioned in an orthogonal arrangement form the SEA 170 in the embodiment shown in FIG. 7. Other embodiments of an IMD incorporating leadless electrodes may include any number of electrodes mounted on or incorporated in housing 152. Multiple subcutaneous electrodes are provided to allow multiple sensing vector configurations.

Electrodes included in SEA 170 are provided with a conformal coating applied using ALD. In particular, the electrodes may be formed having an electrode base that is chemically less stable than a conductive conformal coating applied there over. The electrodes may be formed having a surface enhanced base with a conformal carbide, nitride, or carbonitride coating applied over the base. Alternatively, a conformal coating may be provided as an intermediate coating with a low-polarization coating applied over the conformal coating as described previously.

Electrode assemblies included in SEA 170 are welded into place on the flattened periphery of housing 152. The complete periphery of IMD 150 may be manufactured to have a slightly flattened perspective with rounded edges to accommodate the placement of SEA assemblies. The SEA electrode assemblies are welded to housing 152 (in a manner that preserves hermaticity of the housing 152) and are connected via conductors (not shown in FIG. 7) to internal electronics module 156. SEA 170 may be constructed using electrodes in the form of flat plates, or alternatively, spiral electrodes. SEA 170 may be mounted in a non-conductive surround shroud Examples of electrode assemblies that may be used for constructing SEA 170 are generally described in U.S. Pat. No. 6,512,940 (Brabec, et al.), U.S. Pat. No. 6,522,915 (Ceballos, et al.) or in U.S. Pat. No. 6,622,046 (Fraley, et al.), all of which patents are hereby incorporated herein by reference in their entireties.

Figure 8:
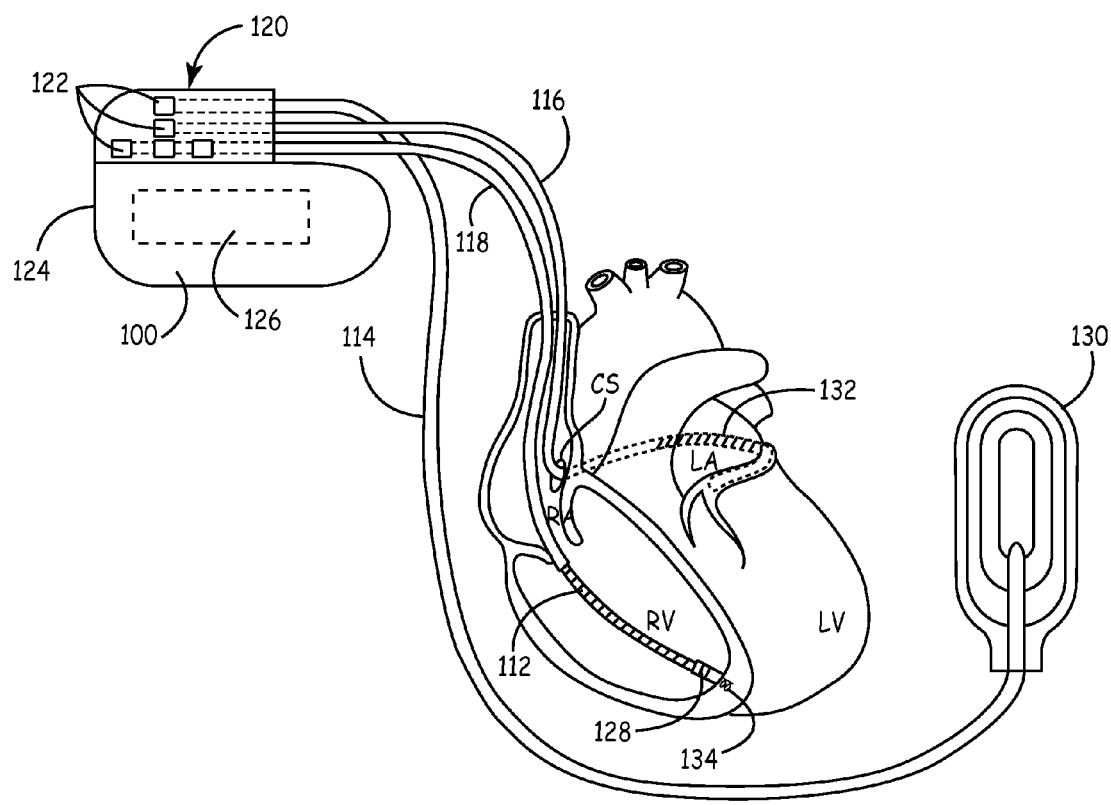
FIG. 8 is a schematic diagram of an IMD and associated leads carrying electrodes implanted in relation to a patient's heart.

FIG. 8 is a schematic diagram of an IMD and associated leads carrying electrodes implanted in relation to a patient's heart. IMD 100 is embodied as an implantable cardioverter defibrillator (ICD) providing sensing of EGM signals and delivering therapeutic electrical stimulation pulses for pacing, cardioverting, and defibrillating the heart as needed. IMD 100 includes a hermetically sealed housing 124 for enclosing an electronics module 126 therein. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality. IMD 100 generally includes a low voltage power source for powering electronics module 126 and one or more high energy density capacitors for generating high voltage cardioversion and defibrillation shocking pulses.

IMD 100 is provided with a connector block 120 formed with one or more connector bores for receiving each of the associated leads 114, 116, and 118 used with IMD 100. Connector block 120 includes electrical contacts 122 which mate with connectors included on proximal connector assemblies included on leads 114, 116, and 118. Electrical contacts 122 are electrically coupled to electronics module 126 via insulated feedthrough conductors extending through IMD housing 124. In this way, various electrodes carried by leads 114, 116, and 118, including tip electrode 134, ring electrode 128, coil electrode 112, coil electrode 132 and subcutaneous patch electrode 130, are electrically coupled to IMD electronics module 126 for carrying out sensing and stimulation functions. Any of the electrodes shown, 112, 128, 130, 132, and 134 may be formed with a conformal coating using ALD.

While a particular IMD is shown associated with cardiac leads adapted to deploy electrodes 112, 128, 130, 132, and 134 in operative relation to the heart, it is recognized that any electrodes carried by leads associated with any IMD, including any pacemakers, ICDs, cardiac or other physiologic monitors, and neurostimulators, may be formed with a conformal coating.

Figure 9:
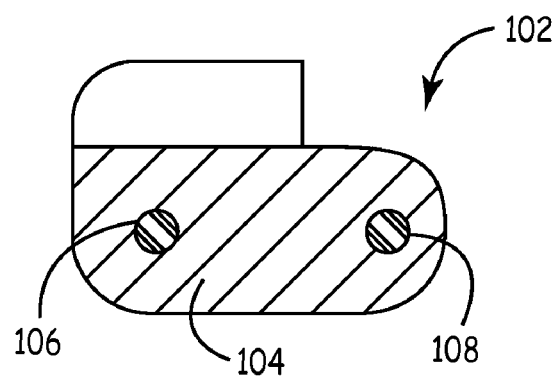
FIG. 9 is a plan view of an IMD housing having a dielectric conformal coated portion patterned with a conductive conformal coated portion.

Furthermore, IMD housing 124 may be provided with a conformal coating applied using ALD methods. A conformal coating applied over a portion of IMD housing 124 may be a conductive or dielectric coating. In FIG. 9, a IMD housing 102 is shown having a dielectric conformal coated portion 104 patterned with a conductive conformal coating applied over portions 106 and 108. Conductively coated portions 106 and 108 may serve as electrodes. Conductive housing 102 is electrically coupled to an electronics module contained therein.

Figure 10:
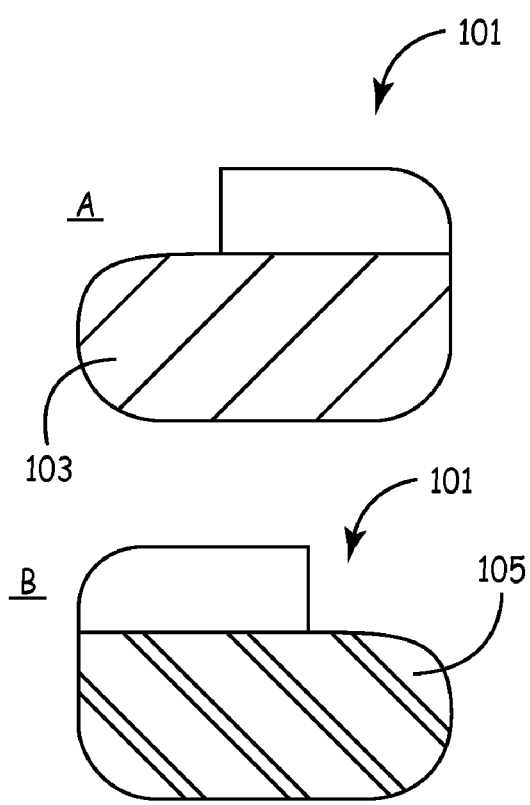
FIG. 10 is a plan view of an IMD housing having a conformal dielectric coating applied using ALD along one face of the IMD housing and a conformal conductive coating applied using ALD along a second face of the IMD housing.

FIG. 10 is a plan view of an IMD housing 101 having a conformal dielectric coating 103 applied using ALD along one face of the IMD housing 101 (see panel A) and a conformal conductive coating 105 applied using ALD along a second face of the IMD housing (see panel B). By depositing dielectric and conductive conformal coatings over selected areas of an IMD housing, conductive portions may be positioned as desired relative to an implant orientation. During the ALD process, portions to be coated with a conductive coating may be masked during deposition of a dielectric coating. Likewise, portions coated with a dielectric coating may be masked during deposition of a conducitve coating. A dielectric coating may be formed as any metal oxide or mixed metal oxide material using a precursor source material and an oxygen source such as water vapor, as described previously. The conductive coating may be formed as described previously as a carbide, nitride, carbonitride of any desired metal or metal alloy.

Figure 11:
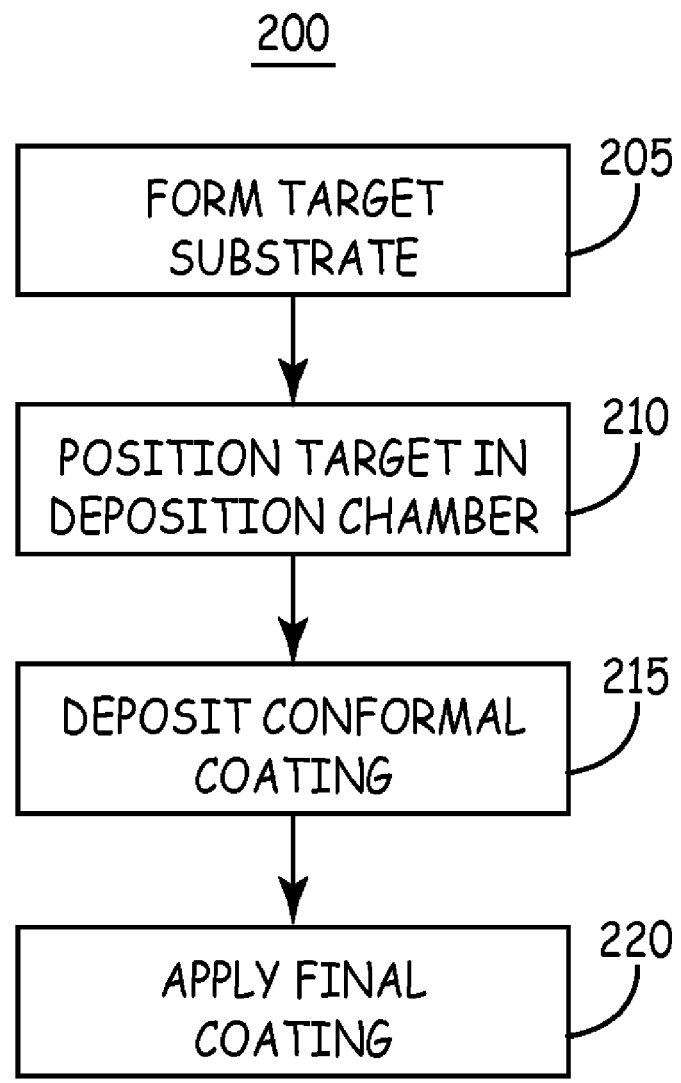
FIG. 11 is a flow chart summarizing a method for manufacturing an implantable medical device having a conformal coating using ALD.

FIG. 11 is a flow chart summarizing a method for manufacturing an implantable medical device having a conformal coating using ALD. At block 205, a conductive base material is selected and formed into a target substrate, which may be an IMD housing or a medical electrode. The substrate is positioned in a deposition chamber at block 210. A conformal coating is applied at block 215 using ALD methods which include rapid succession of alternating gas pulses to deposit the conformal coating one monolayer at a time. The conformal coating may be a dielectric coating, such as a metal oxide or mixed metal oxide, or a conductive coating, such as carbide, nitride, or carbonitride of a selected metal or mixed metals. An optional final coating, such as a low polarization coating, may be applied over the conformal coating at block 220.

Figure 12:
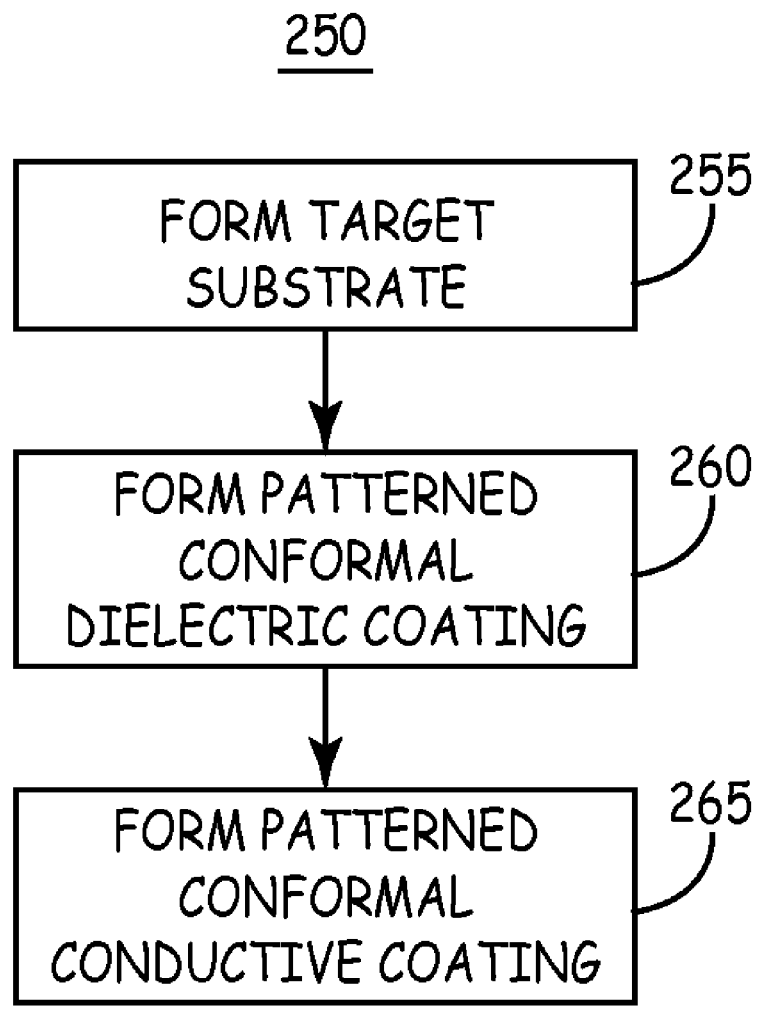
FIG. 12 is a flow chart summarizing a method for manufacturing an implantable medical device according to an alternative embodiment of the invention.

FIG. 12 is a flow chart summarizing a method for manufacturing an implantable medical device according to an alternative embodiment of the invention. At block 255 a target substrate is formed, which may be an electrode base or an IMD housing. At block 260, a patterned, conformal dielectric coating, such as a metal oxide or mixed metal oxide, is formed on the target substrate. A patterned conformal coating may be formed by selective deposition during ALD using litohography techniques, such as soft lithography or photocatalytic lithography, or by decomposing the monolayers using electron beams, ion beams, photolithography, or scanning probe microscopy. At block 265, a patterned conformal conductive coating may additionally or alternatively formed on the substrate surface. In some embodiments, a conductive coating may also be applied over the dielectric coated portions to form capacitive portions of the device.

Thus, implantable medical devices including conformal coatings and methods for manufacturing the same have been presented in the foregoing description with reference to specific embodiments. It is appreciated that various modifications to the referenced embodiments may be made without departing from the scope of the invention as set forth in the following claims.

The invention claimed is:

1. An implantable medical electrical device, comprising:
    a conductive substrate;
    a first conformal conductive coating formed over at least a portion of the substrate, the conductive coating comprising a plurality of atomic monolayers and a low polarization coating applied over the conformal coating;
    an electrical contact; and
    an electronics module adapted to be electrically coupled to the substrate via the electrical contact.

2. The device of claim 1, wherein the conformal coating is more chemically stable than the substrate.

3. The device of claim 1 wherein the substrate is an electrode base and further comprising:
    an elongated insulative lead body, wherein the electrode base is disposed along the lead body, and
    a conductor coupled to the electrode base and extending through the elongated lead body, the conductor being adapted to be electrically coupled to the electrical contact.

4. The device of claim 1 wherein the electrical contact is further electrically coupled to an electrode used for one of sensing electrical body signals and delivering electrical stimulation pulses.

5. The device of claim 4 further comprising a second conformal coating being a conductive coating formed over a second portion of the substrate.

6. The device of claim 1 wherein the substrate comprises one of tungsten, a tungsten alloy, stainless steel, and a stainless steel alloy.

* * * * *